(12) United States Patent
Ouchi

(10) Patent No.: US 7,276,066 B2
(45) Date of Patent: Oct. 2, 2007

(54) MEDICAL INSTRUMENT FOR ENDOSCOPE

(75) Inventor: Teruo Ouchi, Tokyo (JP)

(73) Assignee: PENTAX Corporation, Tokyo (JP)

( * ) Notice: Subject to any disclaimer, the term of this patent is extended or adjusted under 35 U.S.C. 154(b) by 96 days.

(21) Appl. No.: 10/974,827

(22) Filed: Oct. 28, 2004

(65) Prior Publication Data
US 2005/0096650 A1 May 5, 2005

(30) Foreign Application Priority Data
Oct. 29, 2003 (JP) .................. P. 2003-368188
Nov. 10, 2003 (JP) .................. P. 2003-379252

(51) Int. Cl.
*A61B 18/18* (2006.01)
(52) U.S. Cl. .......................... 606/46; 606/47
(58) Field of Classification Search .......... 600/39, 600/104–106, 41–50, 167–171
See application file for complete search history.

(56) References Cited

U.S. PATENT DOCUMENTS

| 3,856,015 A | * | 12/1974 | Iglesias ............ 606/46 |
| 4,311,143 A | * | 1/1982 | Komiya et al. ....... 606/47 |
| 5,078,716 A | | 1/1992 | Doll et al. |
| 5,540,659 A | * | 7/1996 | Teirstein .......... 604/104 |
| 5,794,626 A | * | 8/1998 | Kieturakis ......... 600/567 |
| 6,007,546 A | | 12/1999 | Snow et al. |
| 6,299,612 B1 | | 10/2001 | Ouchi |
| 6,554,850 B1 | | 4/2003 | Ouchi et al. |
| 2001/0009985 A1 | | 7/2001 | Durgin et al. |
| 2001/0044625 A1 | | 11/2001 | Hata et al. |
| 2003/0135222 A1 | | 7/2003 | Baska |

FOREIGN PATENT DOCUMENTS

| EP | 1484025 | 8/2004 |
| JP | 1 118089 | 5/1998 |
| JP | 2002/271128 | 10/2000 |
| JP | 2001/70309 | 3/2001 |
| JP | 2002/153484 | 5/2002 |

OTHER PUBLICATIONS

English Language Abstract of JP10-118089.
U.S. Appl. No. 10/922,956, filed Aug. 3, 2004.
U.S. Appl. No. 10/959,062, filed Oct. 7, 2004.
U.S. Appl. No. 10/962,606, filed Oct. 13, 2004.
English Language Abstract of JP10-118089, Oct. 18, 1996.
English Language Abstract of JP2002/153484.

* cited by examiner

*Primary Examiner*—Roy D. Gibson
(74) *Attorney, Agent, or Firm*—Greenblum & Bernstein, P.L.C.

(57) ABSTRACT

A medical treatment instrument for an endoscope includes: an insulated sheath; a treatment member that is provided at a distal end of the sheath; and a wire loop that surround the treatment member and is capable of expansion and contraction by an operation at a proximal side of the sheath.

10 Claims, 10 Drawing Sheets

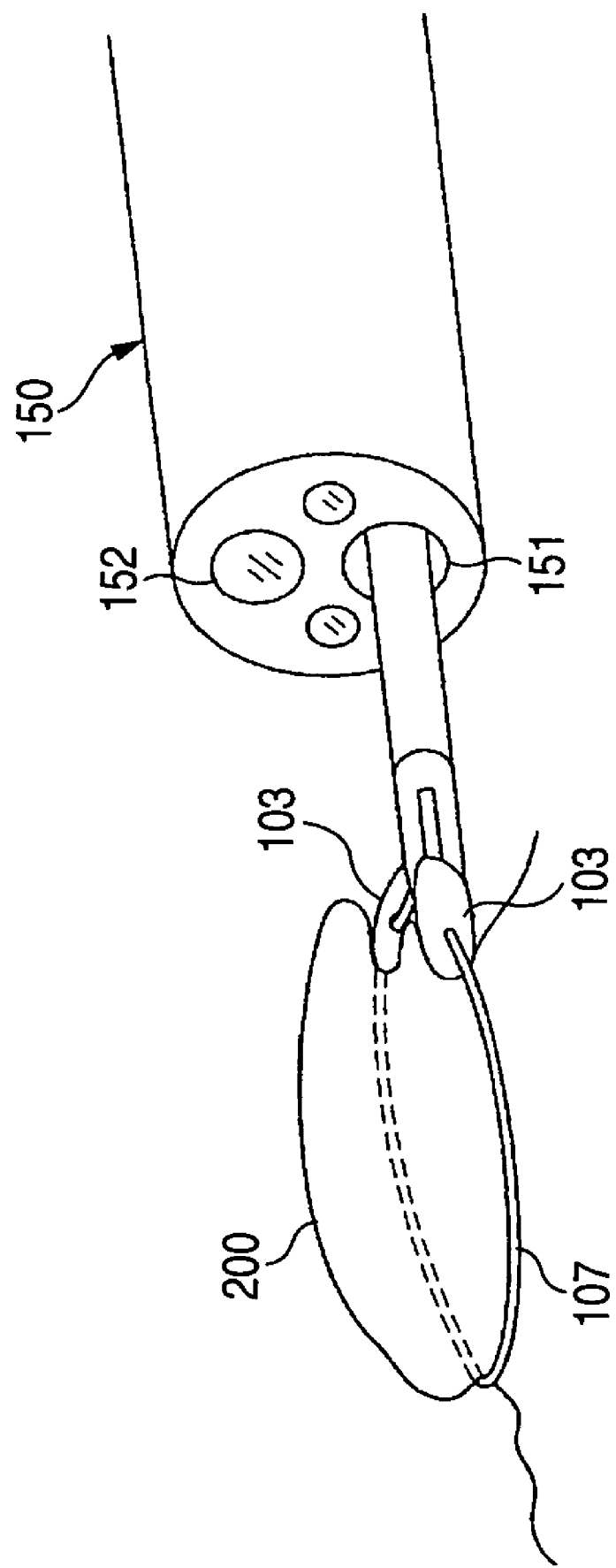

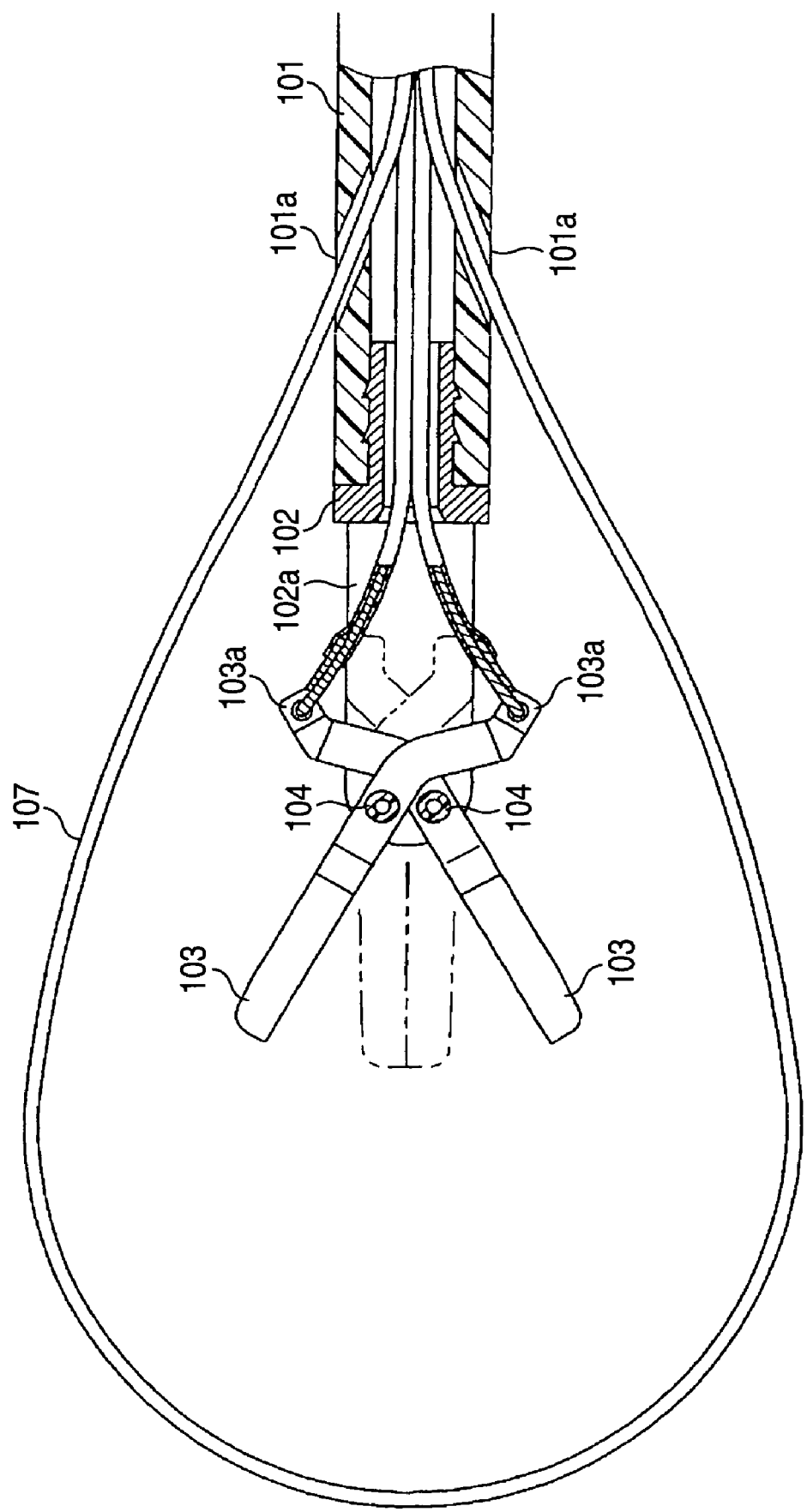

MEDICAL INSTRUMENT FOR ENDOSCOPE

BACKGROUND OF THE INVENTION

The present invention relates to a medical instrument for an endoscope to be passed through a medical instrument insert channel of an endoscope in use, and used for dissection or exsection of mucous tunics of anatomy by distributing high-frequency current.

A medical instrument for an endoscope generally has a structure in which a distal electrode to which high-frequency current can be distributed is projected forward from the distal end of an electrically insulating sheath, whereby mucous tunics or the like which is in contact with the distal electrode is dissected by Joule heat by distributing high-frequency current to the distal electrode which is pressed against the surface of the mucous tunics.

However, when the distal portion of the endoscope is significantly displaced because an operator touches a curved operating knob of the endoscope or because a patient harrumphs and hence the anatomy side is suddenly moved during the operation of high-frequency medical treatment, an unscripted portion of the anatomy may accidentally be dissected.

As a countermeasure to this problem, in the related art, there is a device in which the distal electrode is formed by a flexible metallic strand wire or the like so that the movement of the distal electrode with respect to a diseased part does not occur abruptly, even when the positional relationship between the distal end of the endoscope and the anatomy changes unexpectedly. (For example, JP-A-2002-153484)

When the distal electrode is formed of the metallic strand wire, the distal electrode does not come apart from the dissected portion owing to bending motion of the distal electrode as long as the change of the positional relationship between the distal end of the endoscope and the anatomy is within a certain range, and hence a phenomenon in which dissection of the unscripted portion of the anatomy can be prevented from occurring.

However, when the positional relationship between the distal end of the endoscope and the anatomy is changed unexpectedly by more than several centimeters, the change cannot be absorbed by such bending motion of the distal electrode, and hence there is a risk for dissecting the unscripted portion of the anatomy.

Another kind of a medical instrument for an endoscope is known which is a beak-shaped medical instrument for an endoscope configured in such a manner that a pair of beak-shaped electrodes which are connected to a high-frequency power supply and open and close like a beak by remote control at the proximal end of a sheath are disposed at the distal end of the sheath which is to be inserted into and removed from the medical instrument insert channel of an endoscope. (for example, JP-A-2000-271128)

When performing dissection or the like of anatomy with a beak-shaped medical instrument for an endoscope, an operation including the steps of clamping the anatomy with the beak-shape electrodes to which high-frequency current is distributed, dissecting the same, advancing the instrument a little, closing the same again, and dissecting the same is repeated.

However, when the positional relationship between the distal end of the endoscope and the anatomy is moved unexpectedly and significantly because a patient harrumphs or an operator erroneously operates a curved operating knob of the endoscope when the beak-shaped electrodes are opened or completely closed during such high-frequency operation, it takes a lot of trouble to performing a guiding operation for restoring the beak-shaped electrodes accurately to a portion to be dissected of the diseased part, and hence dissection or exsection of the anatomy may not be performed smoothly.

SUMMARY OF THE INVENTION

Accordingly, it is an object of the present invention to provide a medical instrument for an endoscope in which an distal electrode does not come apart from a diseased part even when the positional relationship between the distal end of the endoscope and the anatomy is changed unexpectedly and significantly during a high-frequency exsectioning operation, so that a high-frequency medical treatment can be performed safely.

It is another object of the present invention to provide a beak-shaped medical instrument for an endoscope in which a beak-shaped electrode does not come apart from a diseased part even when the positional relationship between the distal end of an endoscope and anatomy during the high-frequency operation, and hence the high-frequency operation can be performed smoothly.

In order to solve the aforesaid object, the invention is characterized by having the following arrangement.

(1) A medical treatment instrument for an endoscope comprising:
   an insulated sheath;
   a treatment member that is provided at a distal end of the sheath; and
   a wire loop that surround the treatment member and is capable of expansion and contraction by an operation at a proximal side of the sheath.

(2) The medical treatment instrument according to (1), wherein a pair of through holes are formed on a side wall of the sheath in a vicinity of the distal end of the sheath and a wire constituting the wire loop moves in and out through the through holes so that the wire loop is expanded and contracted.

(3) The medical treatment instrument according to (1), wherein the sheath is adapted to be inserted into and removed from a medical instrument insert channel of the endoscope.

(4) The medical treatment instrument according to (1), wherein
   the treatment member includes an electrode to which high-frequency current is adapted to be distributed, and
   the wire loop is insulated from the electrode.

(5) The medical treatment instrument according to (4), wherein a conductive wire electrically connected to the distal electrode is inserted into and disposed in the sheath, and an operation wire to be operated from the sheath side for causing expansion and contraction of the wire loop is inserted into and disposed in the sheath alongside of the conductive wire so as to be capable of moving in the fore-and-back direction.

(6) The medical treatment instrument according to (4), wherein a portion of the distal electrode projected from the distal end of the sheath is formed into a plate shape, and a surface of the projected plate-shaped portion and the wire loop are substantially flush with each other.

(7) The medical treatment instrument according to (4), wherein an amount of projection of the distal electrode projecting forward from the distal end of the sheath can be adjusted by an operation at the proximal side of the sheath.

(8) The medical treatment instrument according to (7), wherein the distal electrode can be projected from and retracted into the sheath.

(9) The medical treatment instrument according to (4), wherein the distal electrode includes a pair of beak-shaped electrodes which open and close by remote control at the proximal side of the sheath, and wherein the wire loop surrounds a front space to which the pair of beak-shaped electrodes oppose is designed to be expanded and contracted independently from the opening and closing of the pair of beak-shaped electrodes by the operation at the proximal side of the sheath.

(10) The medical treatment instrument according to (9), wherein through holes are formed through the pair of beak-shaped electrodes so as to penetrate therethrough in the opening and closing direction thereof, so that a proximal portions of a wire constituting the wire loop are led through an inner side of the pair of beak-shaped electrodes from the through holes into the sheath, respectively.

(11) The medical treatment instrument according to (1), wherein high-frequency current is adapted to be distributed to the wire loop, and the wire loop is insulated from the electrode.

According to the present invention, since the wire loop is disposed so as to surround the distal electrode so as to be capable of being expanded and contracted by the operation at the proximal side of the sheath, the dissecting operation by the treatment member can be performed by surrounding and lightly tightening the portion around the diseased part to be dissected. Therefore, even when the positional relationship between the distal end of the endoscope and the anatomy is changed unexpectedly and significantly during the high-frequency dissecting operation, the treatment member does not come apart from the diseased part and hence the high-frequency operation can be performed safely.

BRIEF DESCRIPTION OF THE DRAWINGS

FIG. 9 is a perspective view showing a state in which a high-frequency operation is performed using the beak-shaped medical instrument for an endoscope according to the third embodiment of the present invention.

FIG. 10 is a cross-sectional side view of the distal end portion of the beak-shaped medical instrument for an endoscope according to a fourth and fifth embodiments of the present invention.

DETAILED DESCRIPTION OF PREFERRED EMBODIMENTS

Figure 1:
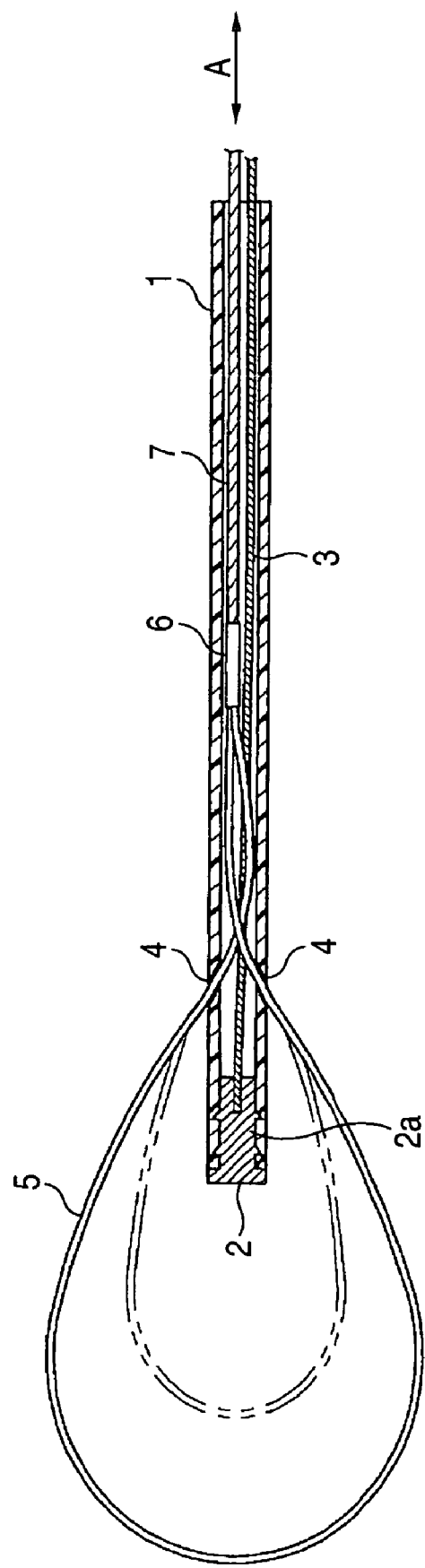
FIG. 1 is a cross-sectional plan view of a distal portion of a medical instrument for an endoscope according to a first embodiment of the present invention.

Referring now to the drawings, embodiments of the present invention will be described.

First Embodiment

Figure 2:
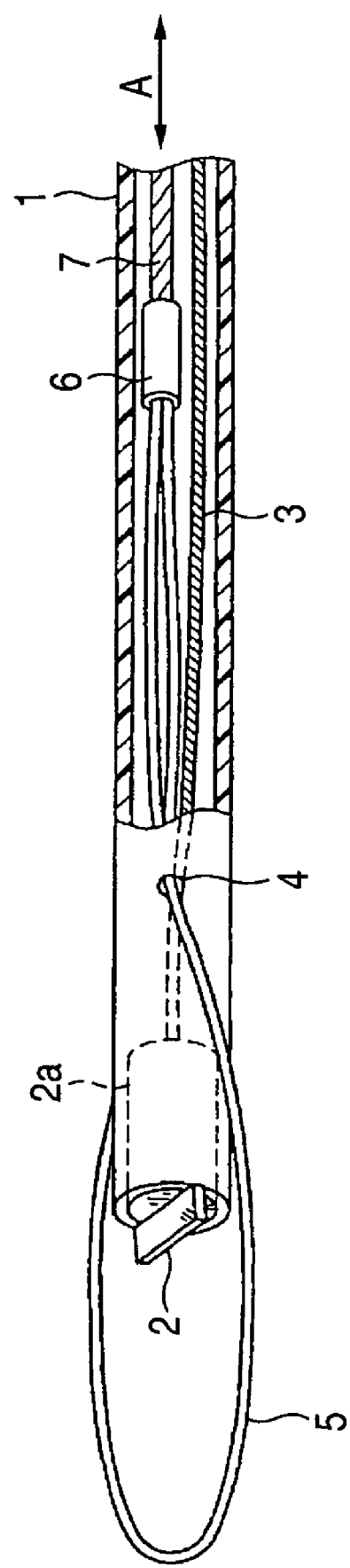
FIG. 2 is a perspective view, partly broken, of the distal portion of the medical instrument for an endoscope according to the first embodiment of the invention.

FIG. 1 is a cross-sectional plan view of a distal portion of a medical instrument for an endoscope according to a first embodiment of the present invention, and FIG. 2 is a perspective view thereof, showing that a flexible sheath 1 to be inserted into or moved from an insertion channel of the medical instrument for an endoscope is formed of an electrically insulating tube such as a Polytetrafluoroethylene tube.

A distal electrode 2 formed of conductive metal is projecting forward from the distal portion of the flexible sheath 1. In this embodiment, the portion of the distal electrode 2 projecting from the flexible sheath 1 is formed into a flat-plate shape, and a cylindrical proximal portion 2a formed integrally therewith is fitted into and fixed to the distal end of the flexible sheath 1. Note that the distal electrode 2 is one of the members constituting a treatment member according to the invention.

The side surface of the proximal portion 2a of the distal electrode 2 is formed with a projection which is bitten into the inner peripheral surface of the flexible sheath 1. However, the structure of fixation of the distal electrode 2 with respect to the flexible sheath 1 may be any other means such as screwing or bonding.

Reference numeral 3 designates a conductive wire for supplying high-frequency current to the distal electrode 2, which is inserted into and disposed in the entire length of the flexible sheath 1 and is bonded at the distal portion thereof to the proximal portion 2a of the distal electrode 2 by soldering or the like. The conductive wire 3 may be either a bare wire or a coated wire.

The side wall of the flexible sheath 1 is formed with a pair of through-holes 4 at symmetrical positions of about 180° from the obliquely front direction respectively, and a wire constituting a wire loop 5 disposed so as to surround the distal electrode is inserted through the pair of through holes 4 into the flexible sheath 1.

The wire loop 5 is formed, for example, of polyester fiber or fluorine contained resin, having heat-resistant property and electrically insulating property, and the positional relationship with respect to the distal electrode 2 is set to be substantially flush with the surface (plate surface) of the distal electrode 2.

The wire constituting the wire loop 5 must simply be electrically insulated with respect to the distal electrode 2, and hence it may be, for example, a fine stainless steel wire covered with a fluorine contained resin tube.

The proximal portions of the wire loop 5 positioned in the flexible sheath 1 are connected to an operating wire 7, which is inserted into and disposed alongside with the conductive wire 3 in the flexible sheath 1 so as to be capable of moving in the fore-and-aft direction, via a connecting pipe 6.

Therefore, by operating the operating wire 7 to move in the fore-and-aft direction as indicated by an arrow A at the proximal side, the wire loop 5 disposed so as to surround the distal electrode 2 at the front of the flexible sheath 1 is expanded and contracted as indicated by a chain double-dashed line in FIG. 1.

Figure 3:
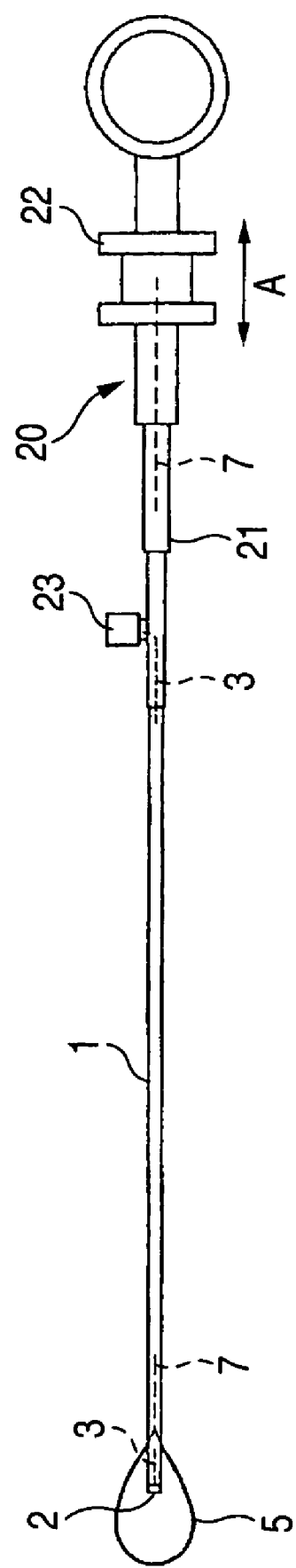
FIG. 3 is a general structure of the medical instrument for an endoscope according to the first embodiment.

FIG. 3 shows a general structure of the medical instrument for an endoscope according to the present embodiment, showing that the side surface of an operating body 21 of a final operating element 20 connected to the proximal end of the flexible sheath 1 is provided with a connecting terminal 23 to which a high-frequency power supply cable, not shown, so as to project therefrom, and the proximal portion thereof is connected to the proximal end of the conductive wire 3. Therefore, by connecting the high-frequency power supply cord to the connecting terminal 23, high-frequency current can be distributed to the distal electrode 2 via the conductive wire 3.

The proximal end of the operating wire 7 is connected to an operating portion 22 disposed at the operating body 21 so as to be slidable. When the operating portion 22 is slid as indicated by the arrow A, the movement thereof is transmitted to the distal side thereof by the operating wire 7 so as to expand and contract the wire loop 5.

Figure 4:
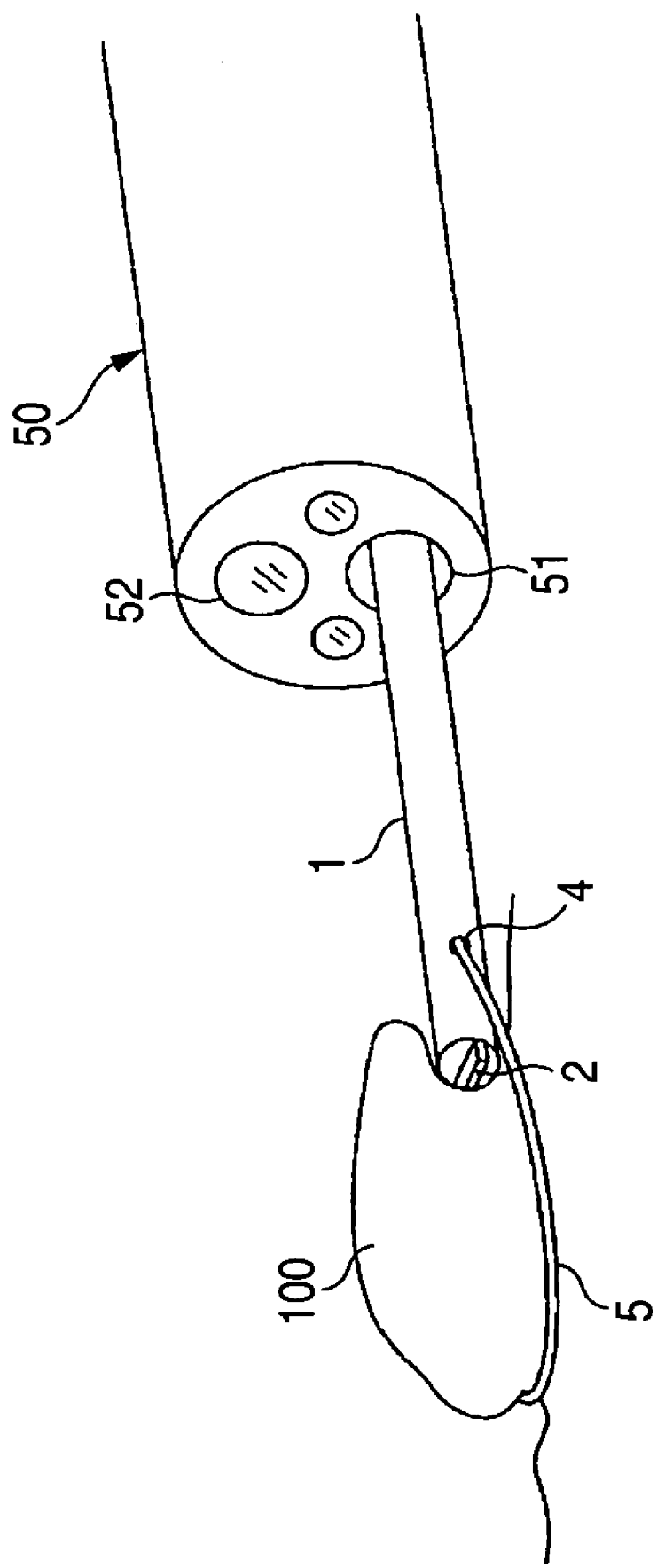
FIG. 4 is a perspective view showing a state of a dissecting operation of mucous tunics with the medical instrument for an endoscope according to the first embodiment of the invention.

When performing a dissecting operation of mucous tunics via the endoscope using the medical instrument for an endoscope configured as described above, as shown in FIG. 4, high-frequency current is distributed in a state in which the distal electrode 2 is pressed against a diseased part 100 in a state in which the diseased part 100 to be dissected is surrounded by and lightly tightened by the wire loop 5, while observing the distal portion of the medical instrument for an endoscope projecting from a medical instrument insertion channel 51 of an endoscope 50.

Accordingly, the mucous tunics of the anatomy to which the distal electrode 2 is in contact is dissected, and even when the positional relationship between the distal end of the endoscope 50 and the diseased part 100 is significantly changed (or apt to be changed) because the operator touches the curved operating knob of the endoscope or the patient harrumphs, since the diseased part 100 is tightened by the wire loop 5, the position of the distal electrode 2 with respect to the diseased part 100 does not change, and hence the high-frequency dissecting operation can be performed safely.

Second Embodiment

Figure 5:
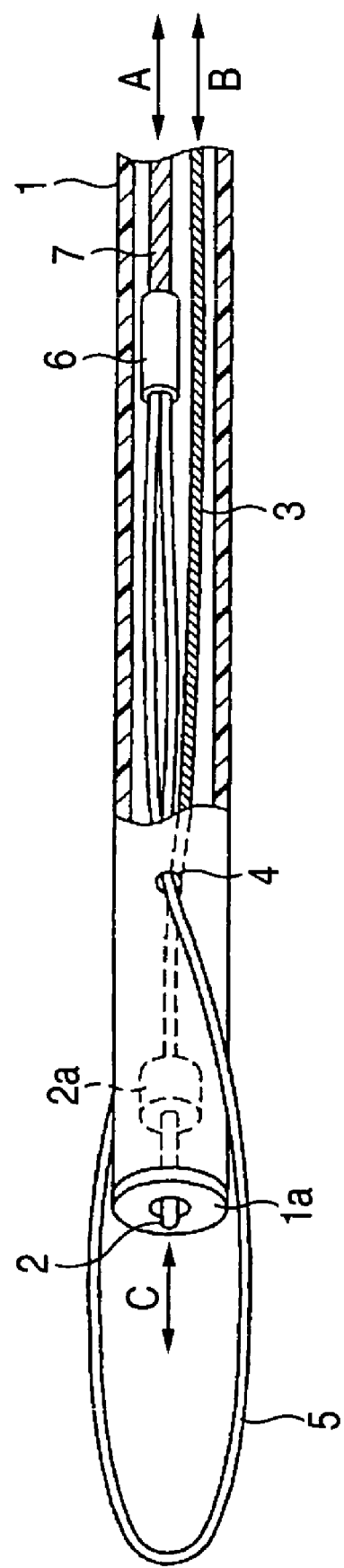
FIG. 5 is a perspective view, partly broken, of the distal portion of the medical instrument for an endoscope according to a second embodiment of the present invention.

FIG. 5 shows a distal portion of the medical instrument for an endoscope according to a second embodiment of the invention, showing that the distal electrode 2 is disposed so as to be capable of moving in the axial direction so as to be projected from and retracted into the distal end of the flexible sheath 1.

In the present embodiment, since the distal electrode 2 is formed into a rod-shape, and the conductive wire 3 is inserted into and disposed within the flexible sheath 1 so as to be capable of moving in the fore-and-aft direction. The distal electrode 2 is disposed so as to pass through the center hole on a lid member 1a attached to the distal end of the flexible sheath 1 so that a stopper 2a formed at the proximal end of the distal electrode 2 comes into abutment of the back surface of the lid member 1a.

Therefore, by operating the conductive wire 3 to move in the fore-and-aft direction as indicated by an arrow B at the distal end, the distal electrode 2 is projected from the distal end of the flexible sheath 1 as indicated by an arrow C, and the amount of projection can be adjusted as desired. At this time, the stopper 2a abuts against the back surface of the lid member 1a, and hence the distal electrode 2 does not project from the distal end of the flexible sheath 1 more than the fixed amount.

Figure 6:
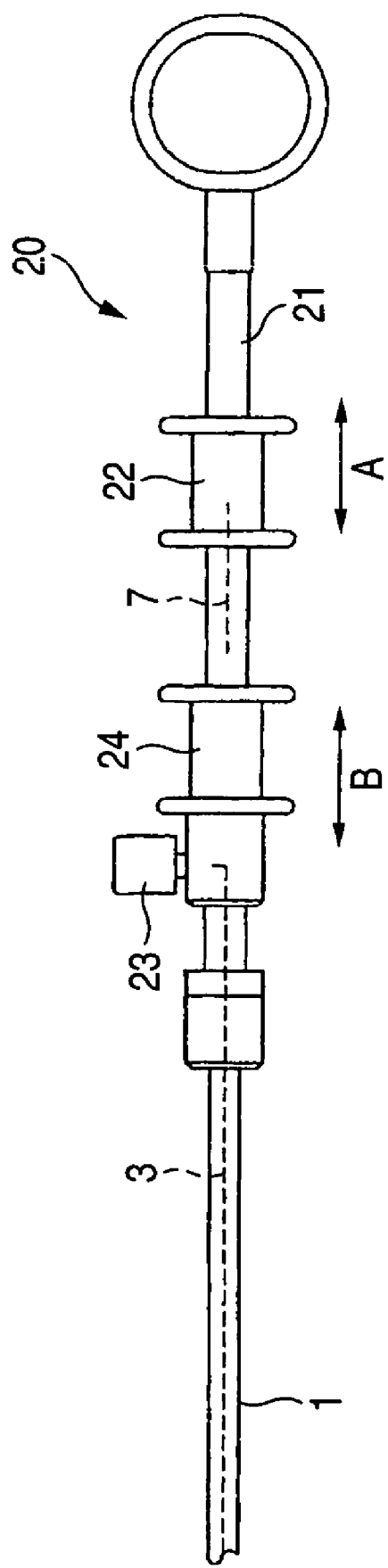
FIG. 6 is a plan view of a final operating element of the medical instrument for an endoscope according to the second embodiment of the invention.

FIG. 6 shows a final operating element 20 for the medical instrument for an endoscope according to the second embodiment, showing that a second operating portion 24 for operating the conductive wire 3 so as to move in the fore-and-aft direction as indicated by the arrow B is slidably mounted to the final operating element body 21, and the connecting terminal 23 is provided on the second operating portion 24.

Third Embodiment

Figure 7:
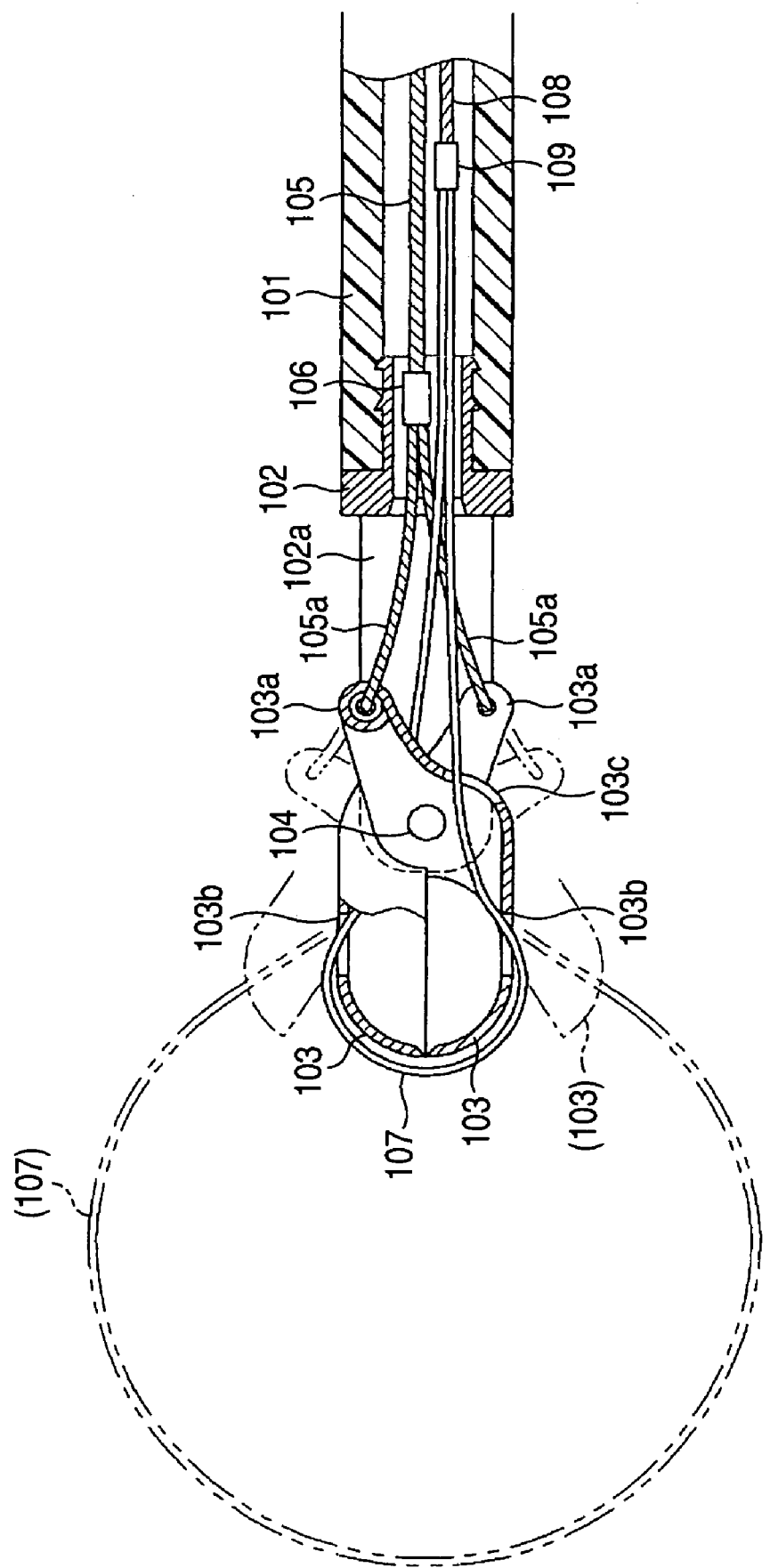
FIG. 7 is a cross-sectional side view of a distal portion of a beak-shaped medical instrument for an endoscope according to a third embodiment.

FIG. 7 shows a distal portion of a beak-shaped medical instrument for an endoscope according to a third embodiment of the present invention, in which a distal end supporting body 102 formed of electrically insulating material such as ceramic is connected to the distal end of a flexible sheath 101 formed of an electrically insulating flexible tube such as a Polytetrafluoroethylene tube.

A pair of beak-shaped electrodes 103 formed of conductive metal such as stainless steel into the shape of a biopsy forceps cup are supported at the position in the vicinity of the distal end of a slit 102a formed along the entire length of the distal end supporting body 102 except for the portion at the rear end by a spindle 104 so as to be capable of opening and closing toward the front like a beak, and drive arms 103a formed integrally with the respective beak-shaped electrodes 103 are disposed within the slit 102a at the position rearwardly of the spindle 104. Note that the pair of beak-shaped electrodes 103 is one of the members constituting the treatment member according to the invention.

A operating wire 105 formed of conductive material for opening and closing the beak-shaped electrodes 103 is inserted into and disposed in the flexible sheath 101 along the entire length thereof so as to be capable of moving forward and backward in the axial direction, and a pair of conductive drive wires 105a bifurcated from the wire 105 and connected by a connecting pipe 106 are connected to the drive arms 103a, respectively.

Therefore, the pair of beak-shaped electrodes 103 can be opened and closed like a beak about the spindle 104 when moving the electrode opening and closing wire 105 in the fore-and-aft direction from the proximal side of the flexible sheath 101, and high-frequency current can be distributed to the respective beak-shaped electrodes 103 via the electrode opening and closing wire 105. In FIG. 7, the closed state of the beak-shaped electrodes 103 is shown by a solid line, and the opened state of the same is shown by a chain double dashed line.

The portions which correspond to the backs and the bottoms of the pair of beak-shaped electrodes 103 are formed with through holes 103b, 103c respectively, so that the proximal portions of a wire of a wire loop 107 formed of synthetic resin wire, such as polyester fiber or fluorine contained resin, having both heat resistance property and electrical insulating property are led through the through holes 103b on the backs of the respective beak-shaped electrodes 103, and then into the flexible sheath 101 through the through holes 103c on the bottoms thereof.

The wire which constitutes the wire loop 107 must simply be electrically insulated from the beak-shaped electrodes 103, and hence may be the stainless steel wire covered by the fluorine resin contained tubes, for example.

The proximal ends (both ends) of the wire loop 107 are connected to a distal end of the wire loop opening and closing wire 108 disposed so as to be capable of moving forward and backward in the axial direction alongside with the electrode opening and closing wire 105 in the flexible sheath 101 via a connecting tube 109.

The wire loop opening and closing wire 108 can be moved forward and backward from the proximal side of the flexible sheath 101 independently from the electrode opening and closing wire 105, and the wire loop 107 is expanded and contracted in conjunction with the forward and backward movement of the wire loop opening and closing wire 108.

In FIG. 7, the contracted state of the wire loop 107 is shown by a solid line, and the expanded state of the same is shown by a chain double-dashed line, The wire loop 107 extends from the through holes 103b formed on the respective beak-shaped electrodes 103 so as to surround the space at the front to which the pair of beak-shaped electrodes 103 oppose.

Figure 8:
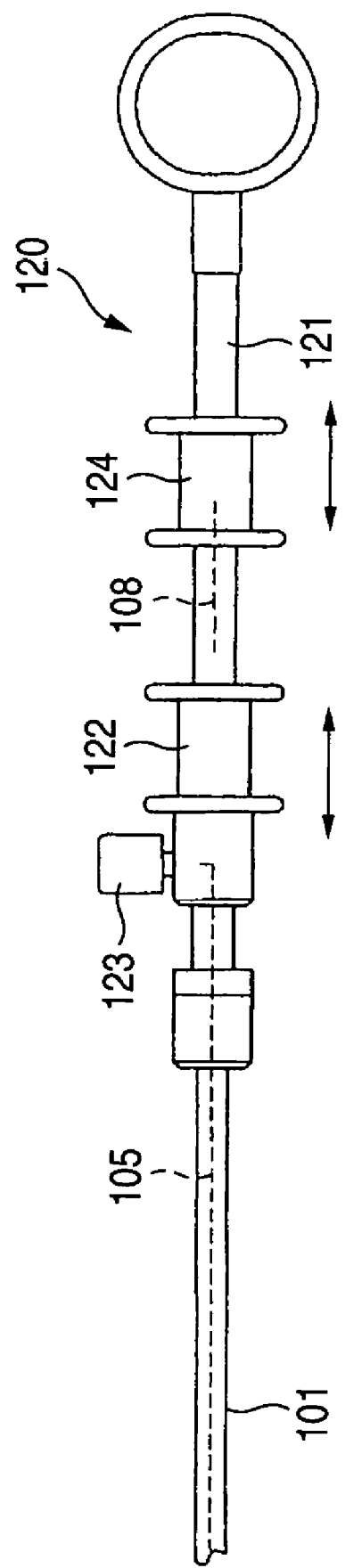
FIG. 8 is a side view of a final operating element of the beak-shaped medical instrument for an endoscope according to the third embodiment of the present invention.

FIG. 8 shows a final operating element 120 provided on the proximal side of the beak-shaped medical instrument for an endoscope of this embodiment, and an electrode opening and closing handle 122 for moving the electrode opening operating wire 105 forward and backward and a wire loop opening and closing portion 124 for moving the wire loop opening and closing wire 108 forward and backward are disposed on a final operating element body 121 so as to be capable of sliding independently from each other.

The electrode opening and closing handle 122 is formed with a connecting terminal 123 to which a high-frequency power supply cable, not shown, is connected so as to project therefrom, and the proximal end of the electrode opening and closing operating wire 105 is connected to the proximal portion thereof. Therefore, by connecting the high-frequency power supply cord is connected to the connecting terminal 123, high-frequency current can be distributed to the beak-shaped electrodes 103 via the electrode opening and closing wire 105.

In this arrangement, when the electrode opening and closing operating handle 122 is operated forward and backward, the pair of beak-shaped electrode 103 are opened and closed via the electrode opening and closing wire 105, and when the wire loop opening and closing operating handle 124 is moved forward and backward, the wire loop 107 is expanded and contracted via the wire loop opening and closing wire 108. These operations can be performed independently from each other.

When performing dissecting operation of mucous tunics via the endoscope using the beak-shaped medical instrument for an endoscope, as shown in FIG. 9, high-frequency current is distributed in a state in which the pair of beak-shaped electrodes 103 clamp a diseased part 200 in a state in which the diseased part 200 to be dissected is surrounded by and lightly tightened by the wire loop 107, while observing the distal portion of the medical instrument for an endoscope projecting from a medical instrument insertion channel 151 of an endoscope 150 via a observation port 152.

Accordingly, even when the positional relationship between the distal end of the endoscope 150 and the diseased part 200 is significantly changed (or apt to be changed) because the operator touches the curved operating knob of the endoscope or the patient harrumphs, when mucous tunics of tissue which is clamped by the beak-shaped electrodes 103 is dissected and the pair of beak-shaped electrodes 103 are completely closed, or when the beak-shaped electrodes 103 are opened subsequently, since the diseased part 200 is tightened by the wire loop 107, the position of the beak-shaped electrodes 103 with respect to the diseased part 200 does not change, and hence the high-frequency dissecting operation can be continued smoothly by moving the beak-shaped electrode 103 forward and then closed.

Fourth Embodiment

FIG. 10 shows a fourth embodiment of the present invention, in which a pair of through holes 1a are formed on a side wall of the flexible sheath 101 in the vicinity of the distal end thereof at the symmetrical positions of about 180° from the obliquely front direction respectively, and the proximal portions of the wire, which constitutes the wire loop 107 are led into the flexible sheath 101 through the respective through holes 101a. In this arrangement, the same operations and effects as the third embodiment described above can be obtained.

In this embodiment, the pair of beak-shaped electrodes 103 are formed into scissors having no cutting edges and are electrically insulated from each other, and one of the beak-shaped electrode 103 is connected to the cathode side of the high-frequency power supply, and the other beak-shaped electrode 103 is connected to the anode side.

As described above, the shape of the beak-shaped electrodes 103 in the present invention may by any type, and may be applied both to the beak-shaped medical instrument for an endoscope of a mono-polar type as in the third embodiment, and the beak-shaped medical instrument for an endoscope of a bipolar type as in the fourth embodiment.

Fifth Embodiment

Because the structure of the fifth embodiment is almost same to that of the fourth embodiment, the fifth embodiment will be described with reference to FIG. 10.

Difference between the fourth embodiment and the fifth embodiment is in the high-frequency current supply. That is, in the fifth embodiment, the high-frequency current is supplied to the wire loop 107 instead of the pair of beak-shaped electrodes 103, and the pair of beak-shaped electrodes 103 is insulated from the wire loop 107.

The operation of the medical treatment according to the fifth embodiment will be described.

When performing dissecting operation of mucous tunics with using the endoscope using the beak-shaped medical instrument according to the fifth embodiment, the pair of beak-shaped electrodes 103 clamps the diseased part and the wire loop 107 lightly tightens the diseased part. Then, the wire loop 107 is contracted by operating the wire at the proximal side of the sheath until the diseased part is dissected from the body while the high-frequency current is applied to the wire loop 107. According to the fifth embodiment, since the pair of beak-shaped electrodes 103 clamp the diseased part while the wire loop 107 dissects the diseased part, the position of the wire loop 107 with respect to the diseased part does not change, and hence the high-frequency dissecting operation can be continued smoothly by contracting the wire loop 107.

Of course, the present invention is not limited to the embodiments described above and shown in the drawings, and can be realized by any modification without departing from the scope of the invention. For example, the medical instrument for an endoscope does not have to be designed to perform the high-frequency dissecting operation, and a cutter for simply cutting the diseased part may be employed as a treatment member provided at a distal end of the sheath.

What is claimed is:

1. A medical treatment instrument for an endoscope comprising:
    an insulated sheath;
    a treatment member provided at a distal end of the sheath;
    a wire loop that surrounds and wraps around a tip of the treatment member, the wire loop being configured for expansion and contraction by an operation at a proximal side of the sheath; and
    a pair of through holes formed on a side wall of the sheath, the pair of through holes extending transversely through the side wall in a vicinity of the distal end of the sheath, and a wire of the wire loop moving in and out through the through holes so that the wire loop is expanded and contracted.

2. The medical treatment instrument according to claim 1, wherein the sheath is configured to be inserted into and removed from a medical instrument insert channel of the endoscope.

3. The medical treatment instrument according to claim 1, wherein the wire loop is configured to receive high-frequency current, the wire loop being insulated from the electrode.

4. A medical treatment instrument for an endoscope comprising:
    an insulated sheath;
    a treatment member provided at a distal end of the sheath;
    a wire loop that surrounds and wraps around a tip of the treatment member, the wire loop being configured for expansion and contraction by an operation wire provided at a proximal side of the sheath; and
    the treatment member including an electrode configured to receive high-frequency current,
    the wire loop being insulated from the electrode.

5. The medical treatment instrument according to claim 4, further comprising a conductive wire electrically connected to the electrode at a center axis of the sheath, and the operation wire configured to be operated from the sheath side so as to cause expansion and contraction of the wire loop, the operation wire being inserted into and disposed in the sheath alongside of the conductive wire so as to be capable of moving in the fore-and-back direction.

6. The medical treatment instrument according to claim 4, wherein a portion of the electrode projecting from the distal end of the sheath is configured to have a plate shape, and a surface of the projecting plate-shaped portion and the wire loop are substantially flush with each other.

7. The medical treatment instrument according to claim 4, wherein an amount of projection of the electrodes, projecting forwardly from the distal end of the sheath, is configured to be adjusted by an operation at the proximal side of the sheath.

8. The medical treatment instrument according to claim 7, wherein the electrode is configured to project from and retract into the sheath.

9. The medical treatment instrument according to claim 4, wherein the electrode includes a pair of beak-shaped electrodes which open and close by remote control at the proximal side of the sheath, and
    wherein the wire loop surrounds a front space opposite the pair of beak-shaped electrodes, the wire loop being configured to expand and contract independently of the opening and closing of the pair of beak-shaped electrodes.

10. The medical treatment instrument according to claim 9, wherein through holes are provided through the pair of beak-shaped electrodes so as to penetrate therethrough in the opening and closing direction thereof, so that proximal portions of a wire of the wire loop are led through an inner side of the pair of beak-shaped electrodes from the through holes into the sheath, respectively.

* * * * *